(12) United States Patent
Zhuang et al.

(10) Patent No.: US 9,146,156 B2
(45) Date of Patent: Sep. 29, 2015

(54) LIGHT SOURCE TRACKING IN OPTICAL METROLOGY SYSTEM

(75) Inventors: Guorong V. Zhuang, Santa Clara, CA (US); Shankar Krishnan, Santa Clara, CA (US); Johannes D. de Veer, Menlo Park, CA (US); Klaus Flock, Mountainview, CA (US); David Y. Wang, Santa Clara, CA (US); Lawrence D. Rotter, Pleasanton, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 300 days.

(21) Appl. No.: 13/285,712

(22) Filed: Oct. 31, 2011

(65) Prior Publication Data

US 2013/0033704 A1 Feb. 7, 2013

Related U.S. Application Data

(60) Provisional application No. 61/502,507, filed on Jun. 29, 2011.

(51) Int. Cl.
*G01B 11/26* (2006.01)
*G01J 3/02* (2006.01)
(Continued)

(52) U.S. Cl.
CPC ............. *G01J 3/0264* (2013.01); *G01J 3/0208* (2013.01); *G01J 3/0278* (2013.01); *G01J 3/06* (2013.01); *G01J 3/10* (2013.01); *G01N 21/4785* (2013.01); *G01B 2210/56* (2013.01)

(58) Field of Classification Search
CPC . G01N 21/4785; G01N 21/274; G01N 21/93; G01N 2201/127; G01J 3/0264; G01J 3/0208; G01J 3/0278; G01J 3/06; G01J 3/10; G01J 2001/086; G01B 2210/56

USPC .......................... 356/138, 150, 400, 614, 620
See application file for complete search history.

(56) References Cited

U.S. PATENT DOCUMENTS 5,700,084 A * 12/1997 Yasukawa et al. ............. 362/275
5,923,020 A * 7/1999 Kurokawa et al. ............. 235/454
(Continued)

FOREIGN PATENT DOCUMENTS

| JP | 08-327554 A | 12/1996 |
| KR | 10-2004-010088 A | 12/2004 |
| WO | WO 2010146799 A1 * | 12/2010 ............. G01N 21/95 |

OTHER PUBLICATIONS

Hamamatsu Photonics, Light Sources, Xenon lamps, mercury-xenon lamps, http://www.hamamatsu.com/us/en/product/category/1001/3011/index.html, Printed online May 6, 2015.

*Primary Examiner* — Michael A Lyons
*Assistant Examiner* — Violeta A Prieto
(74) *Attorney, Agent, or Firm* — Suiter Swantz pc llo

(57) ABSTRACT

The present invention may include loading a diagnostic sample onto a sample stage, focusing light from an illumination source disposed on a multi-axis stage onto the diagnostic sample, collecting a portion of light reflected from a surface of the diagnostic sample utilizing a detector, wherein the illumination source and the detector are optically direct-coupled via an optical system, acquiring a set of diagnostic parameters indicative of illumination source position drift from the diagnostic sample, determining a magnitude of the illumination source position drift by comparing the acquired set of diagnostic parameters to an initial set of parameters obtained from the diagnostic sample at a previously measured alignment condition, determining a direction of the illumination source position drift; and providing illumination source position adjustment parameters configured to correct the determined magnitude and direction of the illumination source position drift to the multi-axis actuation control system of the multi-axis stage.

21 Claims, 10 Drawing Sheets

(51) Int. Cl.
*G01N 21/47* (2006.01)
*G01J 3/06* (2006.01)
*G01J 3/10* (2006.01)

(56) References Cited

U.S. PATENT DOCUMENTS

| | | | |
|---|---|---|---|
| 6,201,601 B1 * | 3/2001 | Vaez-Iravani et al. | 356/237.4 |
| 6,286,969 B1 * | 9/2001 | Kurokawa et al. | 362/11 |
| 6,704,101 B1 * | 3/2004 | Rangarajan et al. | 356/237.2 |
| 6,765,676 B1 * | 7/2004 | Buermann | 356/448 |
| 7,095,498 B2 * | 8/2006 | Horie | 356/364 |
| 7,113,274 B2 * | 9/2006 | Yang et al. | 356/237.1 |
| 7,369,233 B2 * | 5/2008 | Nikoonahad et al. | 356/369 |
| 7,394,551 B2 * | 7/2008 | Harrison | 356/504 |
| 7,511,816 B2 * | 3/2009 | Reich et al. | 356/400 |
| 7,557,919 B2 * | 7/2009 | Fukue | 356/369 |
| 8,559,008 B2 * | 10/2013 | Blasenheim et al. | 356/369 |
| 2004/0150820 A1 | 8/2004 | Nikoonahad et al. | |
| 2006/0256339 A1 * | 11/2006 | Lowney et al. | 356/432 |
| 2008/0111982 A1 * | 5/2008 | Noordman et al. | 355/69 |
| 2010/0039642 A1 * | 2/2010 | Bahatt et al. | 356/328 |
| 2012/0133928 A1 * | 5/2012 | Urano et al. | 356/237.2 |

\* cited by examiner

LIGHT SOURCE TRACKING IN OPTICAL METROLOGY SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled APPARATUS AND METHODS OF LIGHT SOURCE TRACKING IN OPTICAL METROLOGY MEASUREMENT SYSTEM, naming Shankar Krishnan, Guorong Vera Zhuang, Klaus Flock, and Johannes D. de Veer, as inventors, filed Jun. 29, 2011, Application Ser. No. 61/502,507.

TECHNICAL FIELD

The present invention generally relates to a method and system for optically coupling a light source to a broadband spectrometer, and, in particular, a method and system for light source tracking and illumination conditioning in a broadband spectrometer based optical metrology system.

BACKGROUND

Broadband spectrum illumination sources are commonly implemented in spectroscopic based optical metrology tools. Such broadband based metrology tools may be utilized to measure various parameters associated with a given sample, such as a semiconductor wafer or lot of semiconductor wafers. Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etching, deposition, and ion implantation. Multiple semiconductor devices may be fabricated in an arrangement on a single semiconductor wafer and then separated into individual semiconductor devices.

Broadband based metrology systems may include, but are not limited to, spectroscopic ellipsometry, reflectometry, or scatterometry based systems. For example, a broadband based metrology system may include a system such as a rotating polarizer ellipsometry (RPE) or a rotating analyzer ellipsometry (RAE). Typically, a broadband based metrology tool includes one or more broadband light sources, such as a Xenon lamp, illumination optics, a sample stage, collection optics, and one or more detectors. In a general sense, broadband based metrology systems may include an illumination source capable of emanating light within the range of deep ultraviolet (DUV) to near infrared (NIR).

Metrology processes are used at various steps during a semiconductor manufacturing process to monitor and control one or more semiconductor layer processes. For example, broadband based metrology may be used to measure characteristics of a thin film deposited or grown on the surface of a semiconductor wafer, as well as patterned features formed on the semiconductor wafer. By sampling light reflected from a semiconductor wafer at a detector as a function of angle of incidence (AOI), azimuthal angle, polarization, and wavelength, information related to the physical properties of the wafer may be gathered. Such features include, but are not limited to, film thickness, dispersion within the film, wafer structure shapes, and critical dimension (CD) of structures of the wafer.

Typically, the illumination source of a given broadband spectrometry based metrology system is coupled to the collection optics of the system via optical fiber. FIG. 1 illustrates an example of a system implementing optical fiber to couple an illumination source to a portion of the collection optics. The system 100 includes, for example, an optical fiber 102, a pair of mirrors 106a and 106b, and a rotating polarizer 108. In this sense, the optical fiber 102 is utilized to present light 104 from a broadband source (not shown) to the illustrated portion of the collection optics. The utilization of optical fiber to couple a broadband source to collection optics aids in improving pointing stability and intensity fluctuations created due to beam pointing errors. Moreover, optical fiber may act as a light scrambler, causing the intensity spatial distribution of the transmitted light to become more uniform as it propagates through the optical fiber. Further, the spatial dimension of the illumination source (as it is presented to the collection optics) is defined by the physical diameter of the optical fiber. As such, optical fiber plays a key role in both beam shaping and beam stabilization.

The UV throughput capabilities of optical fiber, however, degrade over time, due to solarization and UV enhanced photocontamination. This degradation leads to increased spectral instability and decreased system lifetime. The degradation of UV throughput may lead to a narrowing of the transmitted spectral range, as light below approximately 230 nm (UV boundary) displays reduced transmittance. As such, the UV throughput degradation leads to a modification of the transmitted broadband light. Consequently, it is desirable to provide a system and method that couples a broadband source to collection optics without optical fiber coupling.

SUMMARY

A method for tracking and adjusting illumination source position drift in a broadband spectrometer based optical metrology system is disclosed. In one aspect, a method may include, but is not limited to, loading a diagnostic sample onto a sample stage; focusing light from an illumination source disposed on a multi-axis stage onto the diagnostic sample; collecting a portion of light reflected from a surface of the diagnostic sample utilizing a detector, wherein the illumination source and the detector are optically direct-coupled via an optical system; acquiring a set of diagnostic parameters indicative of illumination source position drift from the diagnostic sample; determining a magnitude of the illumination source position drift by comparing the acquired set of diagnostic parameters to an initial set of parameters obtained from the diagnostic sample at a previously measured alignment condition; determining a direction of the illumination source position drift; and providing a set of illumination source position adjustment parameters configured to correct the determined magnitude and direction of the illumination source position drift to the multi-axis actuation control system of the multi-axis stage. The method may further include conditioning light emanating from the illumination source utilizing a beam conditioning module or an adjustable polarizer slit.

In another aspect, a method may include, but is not limited to, focusing light from an illumination source onto a sample disposed on a sample stage; collecting a portion of light reflected from a surface of the sample utilizing a detector, the illumination source and the detector being optically direct-coupled via an optical system; acquiring one or more images of the illumination source in order to measure at least one of a position of the illumination source or a spatial distribution of light intensity of the illumination emitted by the illumination source; determining illumination source drift by comparing the one or more acquired images of the illumination source to an initial set of images of the illumination source obtained at a previously measured alignment condition; and providing a set of illumination source position adjustment parameters configured to correct the determined illumination source drift to the multi-axis actuation control system. The method may further include conditioning light emanating from the illumination source utilizing a beam conditioning module or an adjustable polarizer slit.

An apparatus for tracking and adjusting illumination source position drift in a broadband spectrometer based optical metrology system is disclosed. In one aspect, an apparatus may include, but is not limited to, a multi-axis actuation control system; an illumination source disposed on a multi-axis actuation stage of the multi-axis actuation control system; a detector, wherein the detector is configured to collect at least a portion of light reflected from a surface of a sample disposed on a sample stage; an optical system including an illumination arm and a detection arm, the illumination source and the detector being optically direct-coupled by the optical system, wherein the illumination arm is configured to focus light emanating from the illumination source onto the surface of the sample, wherein the detection arm is configured to transmit a portion of light reflected from the surface of the one or more specimens to the detector, the illumination arm including a polarizing element and one or more optical focusing elements, the detection arm including an analyzing element and one or more optical collection elements; and a computer system communicatively coupled to the multi-axis actuation control system and the detector, wherein the computer system is configured to: acquire a set of diagnostic parameters from a diagnostic sample disposed on the sample stage, wherein the set of diagnostic parameters are indicative of position drift of the illumination source as measured relative to one or more components of the optical system; determine a magnitude of illumination source position drift by comparing the acquired set of diagnostic parameters to an initial set of parameters obtained from the diagnostic sample at a previously measured alignment condition; determine a direction of illumination source position drift; and provide a set of illumination source position adjustment parameters configured to correct the determined magnitude and direction of the illumination source position drift to the multi-axis actuation control system. In one embodiment, the apparatus may further include a conditioning module positioned between the illumination source and the polarizing element of the illumination arm, wherein the conditioning module is configured to project an image of the illumination source having a selected level of uniformity onto a portion of one or more optical elements of the illumination arm. In another embodiment, the apparatus may further include an adjustable optical slit positioned between the illumination source and the polarizing element of the illumination arm, the adjustable optical slit being communicatively coupled to the computer system, wherein the adjustable slit is configured to adjust in response to instructions received from the computer system.

An apparatus for tracking and adjusting illumination source position drift is disclosed. In one aspect, an apparatus may include, but is not limited to, a multi-axis actuation control system; an illumination source disposed on a multi-axis actuation stage of the multi-axis actuation control system; a detector, the illumination source and the detector being optically direct-coupled, wherein the illumination detector is configured to collect at least a portion of light reflected from a surface of a sample disposed on a sample stage; an optical system including an illumination arm and a detection arm, wherein the illumination arm is configured to focus light emanating from the illumination source onto a surface of one or more specimens, wherein the detection arm is configured to transmit a portion of light reflected from the surface of the sample to the detector, the illumination arm including a polarizing element and one or more optical focusing elements, the detection arm including an analyzing element and one or more optical collection elements; a direct imaging system configured to measure at least one of a position of the illumination source or a spatial distribution of light intensity of the illumination emitted by the illumination source; a computer system communicatively coupled to the multi-axis actuation control system, the direct imaging system, and the detector, wherein the computer system is configured to: determine illumination source position drift by comparing the one or more acquired images of the illumination source to one or more images of an initial set of images of the illumination source obtained at a previously measured alignment condition; and provide a set of illumination source position adjustment parameters configured to correct the determined illumination source drift to the multi-axis actuation control system. In one embodiment, the apparatus may further include a conditioning module positioned between the illumination source and the polarizing element of the illumination arm, wherein the conditioning module is configured to project an image of the illumination source having a selected level of uniformity onto a portion of one or more optical elements of the illumination arm. In another embodiment, the apparatus may further include an adjustable optical slit positioned between the illumination source and the polarizing element of the illumination arm, the adjustable optical slit being communicatively coupled to the computer system, wherein the adjustable slit is configured to adjust in response to instructions received from the computer system.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1:
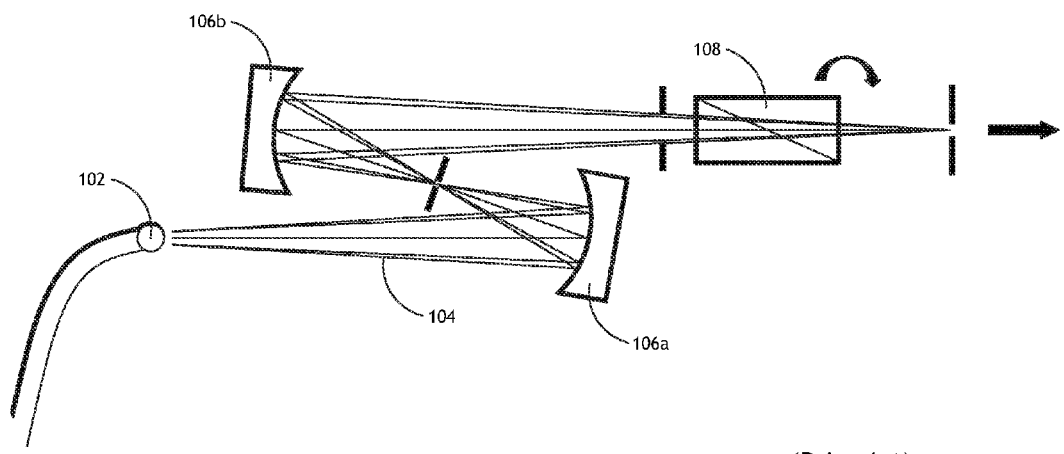
FIG. 1 illustrates a schematic view of an optical fiber coupled illumination source and sample surface as known in the prior art.

Reference will now be made in detail to the subject matter disclosed, which is illustrated in the accompanying drawings.

Referring generally to FIGS. 2A through 5, systems for tracking and adjusting illumination source position drift in a broadband spectrometer based optical metrology system are described in accordance with the present disclosure.

FIG. 2 illustrates a schematic view of a system 200 for tracking and adjusting illumination source position drift in a broadband spectrometer based optical metrology system, in accordance with one embodiment of the present invention. It is recognized herein that long term stability of a measurement system (e.g., optical metrology system) may be measured using measurement results acquired over a period of extended time, such as weeks or months. In this manner, the stability of the measurement system may be acquired and monitored by analyzing measurement results obtained under identical measurement conditions (e.g., identical recipes) as a function of time. Those skilled in the art will further recognize that changes in the measurement results as a function of time may be influenced by numerous factors. The factors may include, but are not limited to, illumination source position relative to the optical system, slow decay of illumination source intensity, and changes in sample conditions, such as changes in optical properties of the measured sample (e.g., optical changes due to accumulated UV exposure).

As used throughout the present disclosure, the term "direct coupling" generally refers to a configuration wherein light from an illumination source is delivered to a measurement system (e.g., detector) through free space (i.e., no intervening transmission medium, such as an optical fiber). The direct free space coupling may take place in vacuum, an ambient atmosphere, or a purged environment (e.g., inert gas purge). The implementation of a direct-coupled illumination-detector system may lead to instabilities in the position of the illumination source relative to the measurement optics of the system 200. It is generally desirable to maintain the relative position of the illumination source with respect to the measurement optics, allowing for long term measurement system stability.

The present disclosure is directed toward systems and methods for active tracking of an illumination source of an optical based measurement system. Application of an active illumination source tracking function may enable the system 200 to adjust the spatial positioning of the illumination source relative to the various optical components of the measurement system. It is contemplated herein that the active illumination source tracking function may be executed via a closed-loop feedback operation.

It is contemplated herein that each of the various systems (e.g., system 200, 300, 400, or 500) of the present disclosure may be configured to operate as a broadband spectrometer. For example, the systems of the present disclosure may be configured to operate as a broadband spectral ellipsometer or scatterometer. Further, the systems of the present disclosure may be configured to operate as a polarized or unpolarized spectral reflectometer. Those skilled in the art should recognize that the specific arrangement of system elements may vary depending on the application in question. As such, the specific geometry illustrated in the various should not be interpreted as a limiting, but merely as illustrative in nature.

As shown in FIG. 2, the system 200 may include an illumination source 202 disposed on a multi-axis actuation stage 204 of a multi-axis actuation control system 205, a detector 206 configured to collect light reflected from the surface of a sample 210 (e.g., diagnostic sample) disposed on a sample stage 212, and a computer system 208 communicatively coupled to the actuation control system 205 and the detector 206. The computer system 208 may be configured to receive one or more signals from the detector 206 indicative of intensity measurement data obtained from a diagnostic sample. The computer system 208 may further be configured to transmit one or more instruction signals to the multi-axis actuation control system 205 based on a source position diagnostic algorithm 217, as will be discussed in greater detail further herein. In addition, the system 200 may include an optical system 207 configured to direct-couple the illumination source 202 and the detector 206.

In one aspect of the present invention, the optical system 207 of the system 200 may include an illumination arm 209 and a detection arm 211. The illumination source 202 and the detector 206 may be optically direct-coupled via the illumination arm 209 and the detection arm 211 of the optical system 207. In this manner, light may emanate from the illumination source 202 and travel along the illumination arm 209 to the surface of the sample 210. Light reflected from the sample 210 may then travel from the surface of the sample 210 to the detector 206 along the detection arm 211.

In one embodiment, the illumination arm 209 may include a polarizer 218. It is recognized herein that the polarizer 218 of the illumination arm 209 may include any polarizer known in the art. For example, the polarizer 218 may include a rotating polarizer, such as but not limited to, a Rochon prism. In another example, the polarizer 218 of the illumination arm 209 may include a beam displacer. Further, the detection arm 211 of the optical system 207 may include a corresponding analyzer 224.

In another embodiment, the illumination arm 209 and/or the detection arm 211 may include, but are not limited to, one or more optical elements, 220 and 1222. Those skilled in the art should recognize that numerous optical elements 220, 1222 may be utilized within the illumination arm 209 or detection arm 211 within the scope of the present invention. For example, the optical elements 220 of the illumination arm 209 may include, but are not limited to, a compensator, one or more lenses (e.g., focusing lenses), one or more filters, or one or more collimators. Similarly, the optical elements 222 of the detection arm may include, but are not limited to, a compensator, one or more lenses (e.g., imaging lenses), one or more filters, or one or more collimators.

In another aspect of the present invention, the Illumination source 202 may include any broadband illumination source known in the art. In one embodiment, the illumination source 202 may include, but is not limited to, a halogen light source (HLS). For instance, the halogen light source may include, but is not limited to, a tungsten based halogen lamp. In another example, the illumination source 202 may include a Xenon arc lamp. By yet another example, the illumination source 202 may include a deuterium arc lamp. In a general sense, any illumination source capable of producing illumination in the visible, infrared, and ultraviolet spectral ranges is suitable for implementation in the present invention. For example, a xenon arc lamp is capable of delivering light in a spectral range of 190 nm to 2000 nm, with a gradual radiant intensity decrease below 400 nm. It should be recognized by those skilled in the art that the above described illumination sources do not represent limitations, but should merely be interpreted as illustrative. In another embodiment, the illumination source 202 may include, but is not limited to, any discharge plasma source known in the art. In yet another embodiment, the illumination source 202 may include, but is not limited to, a laser-driven plasma source.

It is noted that the above description relating to the various type of illumination sources should not be interpreted as limiting, but rather merely as illustrative. Those skilled in the art should recognize that any broadband illumination source is suitable for implementation in the present invention. Moreover, it is further contemplated herein that two or more broadband illumination source may be combined in order to tailor to a required broadband spectral range. In this manner, a first source emitting illumination in a first spectral range may be combined with a second source emitting illumination in a second spectral range.

In another aspect of the present invention, the detector 206 may include any light detection system known in the art suitable for implementation in a broadband spectrometer, ellipsometer, reflectometer, or scatterometer setting. In a general sense, any detector capable of measuring spectra across the visible, infrared, and ultraviolet spectral ranges is suitable for implementation in the present invention.

In another aspect of the present invention, the multi-axis stage 204 may include any actuation stage known in the art. For example, the multi-axis actuation stage 204 may include a translational stage or rotational stage. For instance, the multi-axis actuation stage 204 may include, but is not limited to, a motorized translational stage. In another instance, the multi-axis actuation stage 204 may include, but is not limited to, a motorized rotational stage. It is further contemplated herein that the multi-axis actuation stage 204 may consist of a stage having both translational and rotational capabilities.

In a further embodiment, the multi-axis stage 204 may include any stage known in the art capable of responding to a control system from one or more computer systems 208. In this sense, the multi-axis stage 204 may be configured to receive command signals either directly or indirectly from the one or more computer systems 208. For example, the multi-axis stage 204 may be communicatively coupled to the computer system 208, allowing the computer system 208 to directly control the multi-axis stage 204. In another example, the multi-axis control system 205 may control the multi-axis stage 204 using information transmitted from the one or more computer systems 208 to the multi-axis control system 205.

In another aspect of the present invention, the computer system 208 may be configured to execute a source position diagnostic algorithm 217 utilizing information received from a diagnostic sample by the detector 206. In this manner, the detector 206 may acquire a set of intensity measurement data associated with light reflected from a diagnostic sample loaded onto the sample stage 212.

Those skilled in the art will recognized that the measured intensity of the light reflected from the sample 210 (e.g., diagnostic sample) may vary with respect to a variety of parameters. In the case of rotating polarizer ellipsometry, the measured intensity of illumination is expressed by:

$$I = I_0(\alpha \cdot \cos 2P + \beta \cdot \sin 2P) \quad \text{(Eq.1)}$$

$$P = \omega \cdot t \quad \text{(Eq.2)}$$

where I represents the measured intensity by the detector 206, $I_0$ represents the intensity of the light emanating from the illumination source 202, P represents the polarizer angle, and $\omega$ represents the polarizer angular frequency.

Figure 2A:
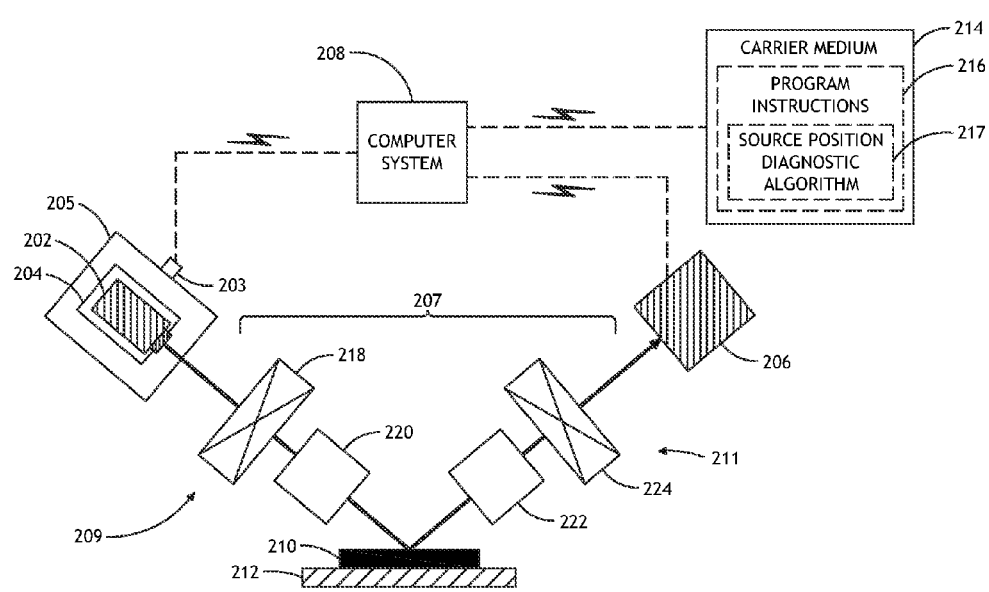
FIG. 2A illustrates a schematic view of a system for tracking and adjusting illumination source position drift in a broadband spectrometer based optical metrology system, in accordance with one embodiment of the present invention.
Figure 2B:
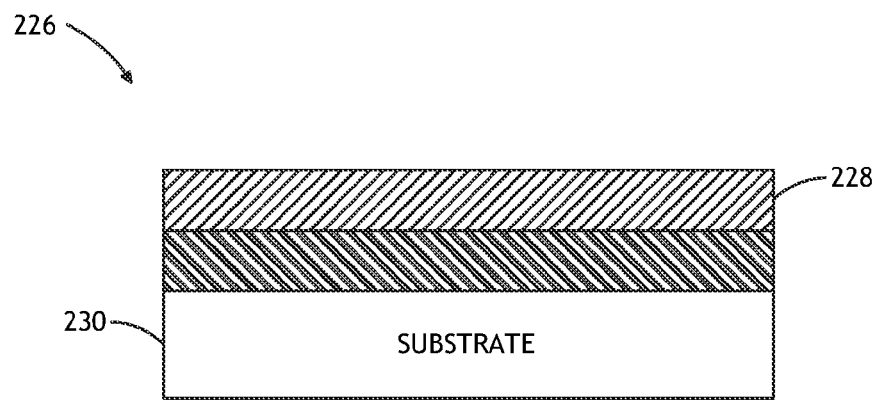
FIG. 2B illustrates a schematic view of a thin film based diagnostic sample suitable for implementation in the system for tracking and adjusting illumination source position drift in a broadband spectrometer based optical metrology system, in accordance with one embodiment of the present invention.
Figure 2C:
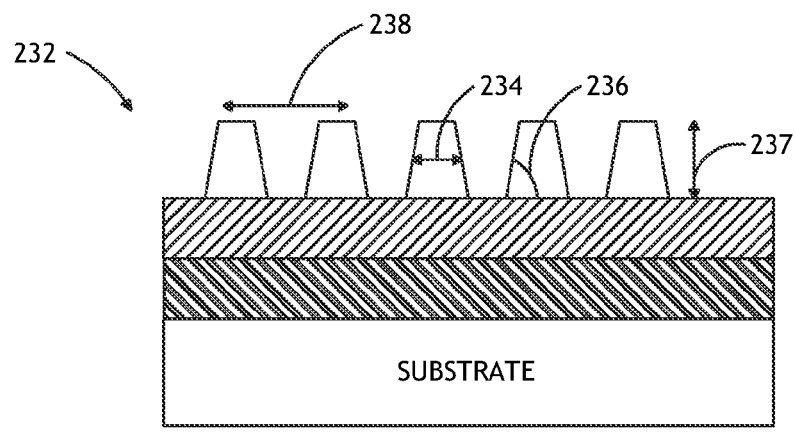
FIG. 2C illustrates a schematic view of a patterned grating based diagnostic sample suitable for implementation in a system for tracking and adjusting illumination source position drift in a broadband spectrometer based optical metrology system, in accordance with one embodiment of the present invention.

As shown in FIGS. 2B and 2C, the diagnostic sample utilized to acquire the diagnostic parameters may include a sample engineered to have a selected set of properties. In one embodiment, the diagnostic sample may include, but is not limited to, a thin film sample 226, having known properties such as, but not limited to, thickness and index of refraction(s). For example, the thin film sample 226 may include a simple film 228 deposited on a substrate 230. For instance, the thin film 228 may consist of a first layer of material and a second layer, each with known properties. In another embodiment, the diagnostic sample may include, but is not limited to, a patterned grating sample 232 deposited on a substrate 230. For example, the patterned grating sample 232 may be constructed to possess a set of selected characteristics. For instance, the selected characteristics of the patterned grating sample 232 may include, but are not limited to, a selected critical dimension (CD) 234, a selected side-wall angle (SWA) 236, a selected feature height 237, or a selected feature periodicity (d) 238.

Upon receiving the measurement results associated with the chosen diagnostic sample, the computer system 208 may acquire a set of diagnostic parameters utilizing the source position diagnostic algorithm 217. The measured set of diagnostic parameters may then be compared to an initial set of diagnostic parameters obtained from the diagnostic sample at an initial set of alignment conditions (e.g., optimal or near-optimal alignment conditions) in order to determine the magnitude of the illumination source 202 position change. In this sense, the computer system 208 may compare diagnostic parameters extracted from intensity data of the diagnostic sample to archived diagnostic sample imagery data taken at an earlier time. For instance, the archived imagery data of the diagnostic sample may be saved in the memory of the computer. Further, it is recognized herein that the archived imagery data of the diagnostic sample may represent imagery data of the diagnostic sample obtained at optimum alignment conditions.

It is recognized herein that the illumination source 202 position drift, which occurs over time, may manifest itself in the measured light intensity data as well as the measured diagnostic parameters. While the source intensity is a convolution of normal illumination source 202 intensity decay and illumination source 202 position drift relative to the measurement optics, it is recognized herein that the diagnostic parameters are a gauge of the illumination source 202 position drift. As such, the diagnostic parameters (when compared to diagnostic parameters obtained at initial alignment conditions) may be utilized to monitor and compensate for the illumination source 202 position drift and change in illumination source 202 intensity spatial distribution.

In the case of the thin film sample 226, the one or more diagnostic parameters that may be extracted may include, but are not limited to, total intensity integrated over a selected spectral range (e.g., intensity integrated over a broad spectrum range), the polarizer asymmetry parameter, or the percentage of higher harmonic components (commonly referred to as "4P"). Each of these diagnostics parameters may be computationally extracted from the spectra obtained from the thin film sample 226 utilizing the computer system 208. After these diagnostic parameters are extracted they may be compared to the diagnostic parameters extracted from the diagnostic sample at an alignment condition (e.g., optimal alignment condition) in order to determine the magnitude of the illumination source 202 drift relative to the initial alignment condition.

In the case of the patterned grating sample 232, diagnostic parameters may be extracted from the acquired spectrum by comparing the experimental data to an accepted theoretical model. In this manner, the experimental data may be regressed against the theoretical model, allowing for the extraction of the diagnostic parameters by the computer system 208. It is recognized herein that, in the event the position of the illumination source shifts relative to an initial measurement instance, the regressed diagnostic parameters, such as SWA, CD, and periodicity of the grated sample 232, may deviate from the diagnostic parameters measured during the initial measurement, allowing the system 200 to determine the magnitude of the illumination source 202 drift.

Upon determining the magnitude of the illumination source 202 drift, the one or more computer systems 208 may then determine the direction of the illumination source position drift. The computer system 208 may transmit one or more instruction signals to the multi-axis control system 205 in order to actuate (e.g., translate) the illumination source 202 (via the actuation stage 204) by the determined magnitude of illumination source position drift in a first direction within the optical plane and in a second direction perpendicular to the optical plane. In this sense, the detector 206 may measure intensity changes as a function of the directed actuation from the computer system 208 and transmit those changes to the computer system 208. The computer system 208 may then deduce the direction of the illumination source 202 position drift utilizing the measurement results from the detector 206.

Upon determining both the magnitude and direction of illumination source 202 position drift, the computer system 208 may transmit a set of illumination source position adjustment parameters to the multi-axis actuation control system 205 via the input 203 of the control system 205. In turn, the multi-axis actuation control system 205 may adjust the position of the multi-axis actuation stage 204 in accordance with the adjustment parameters provided by the computer system 208. In this regard, the adjustment parameters may be used by the control system 205 and the multi-axis stage 204 to compensate for illumination source drift and/or changes in illumination spatial distribution.

It is further contemplated herein that upon compensating for the illumination source position drift and/or changes in illumination spatial distribution, the system 200 may repeat the diagnostic sequence described above. In this manner, the computer system 208 may repeat the source position diagnostic algorithm 217 in an effort to refine the compensation of the illumination source position drift.

It should be recognized that the various steps described throughout the present disclosure may be carried out by a single computer system 208 or, alternatively, a multiple computer system 208. Moreover, different subsystems of the system 200, such as the multi-axis control system 205, may include a computer system suitable for carrying out at least a portion of the steps described above. Therefore, the above description should not be interpreted as a limitation on the present invention but merely an illustration. Further, the one or more computer systems 208 may be configured to perform any other step(s) of any of the method embodiments described herein.

In another embodiment, the computer system 208 may be communicatively coupled to the multi-axis actuation control system 205 or detector 206 in any manner known in the art. For example, the computer system 208 may be communicatively coupled to the multi-axis actuation control system 205 or the detector via a wireline or wireless connection.

For example, the one or more computer systems 208 may be coupled to a computer system of the multi-axis actuation control system 205. Moreover, the computer system 208 of the system 200 may be configured to receive and/or acquire data or information from other systems by a transmission medium that may include wireline and/or wireless portions. In this manner, the transmission medium may serve as a data link between the computer system 208 and other subsystems of the system 200. Moreover, the computer system 208 may send data to external systems via a transmission medium.

The computer system 208 may include, but is not limited to, a personal computer system, mainframe computer system, workstation, image computer, parallel processor, or any other device known in the art. In general, the term "computer system" may be broadly defined to encompass any device having one or more processors, which execute instructions from a memory medium.

Program instructions 216 implementing methods such as those described herein may be transmitted over or stored on carrier medium 214. The carrier medium may be a transmission medium such as a wire, cable, or wireless transmission link. The carrier medium may also include a storage medium such as a read-only memory, a random access memory, a magnetic or optical disk, or a magnetic tape.

The embodiments of the system 200 illustrated in FIG. 2A may be further configured as described herein. In addition, the system 200 may be configured to perform any other step(s) of any of the method embodiment(s) described herein.

Figure 3A:
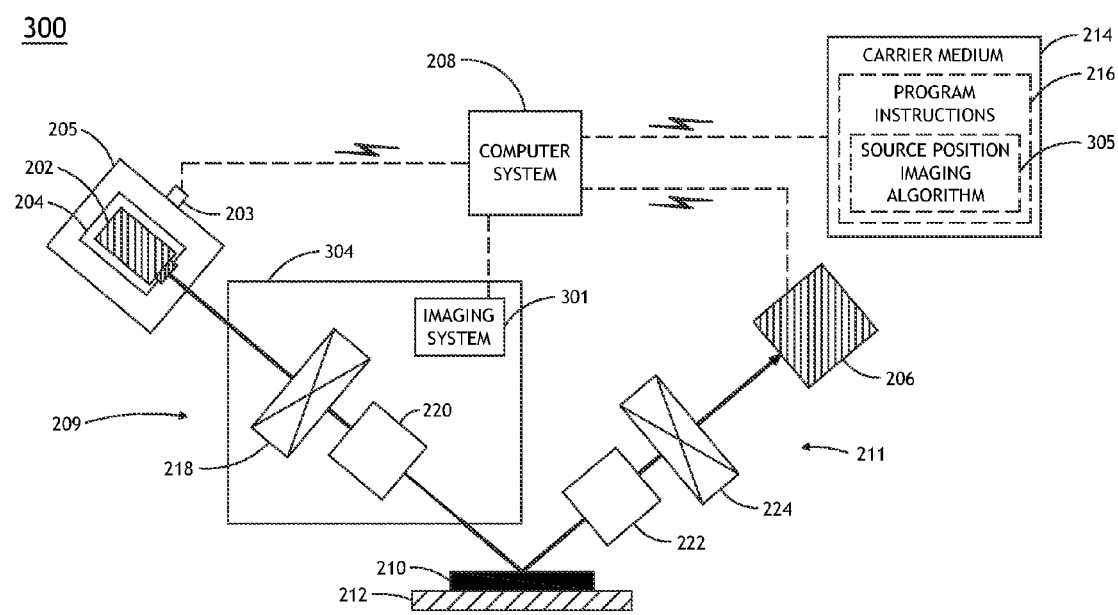
FIG. 3A illustrates a schematic view of a system for tracking and adjusting illumination source position drift in a broadband spectrometer based optical metrology system, in accordance with an alternative embodiment of the present invention.
Figure 3B:
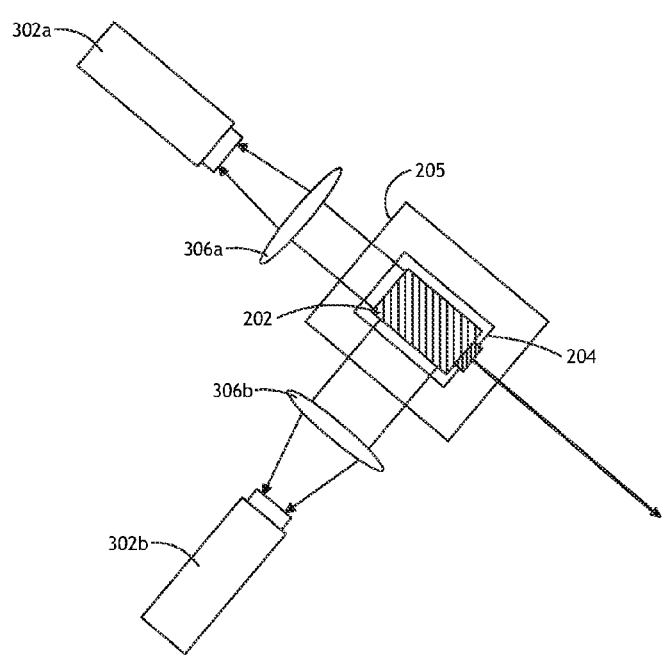
FIG. 3B illustrates a schematic view of a direct imaging system equipped with two cameras and a translatable multi-axis sample stage suitable for implementation in a system for tracking and adjusting illumination source position drift in a broadband spectrometer based optical metrology system, in accordance with an alternative embodiment of the present invention.

FIGS. 3A and 3B illustrate a schematic view of a system 300 for tracking and adjusting illumination source position drift, in accordance with an alternative embodiment of the present invention. In one aspect, the system 300 may include a direct imaging system 301 configured to measure the position of an illumination source 202 or the spatial distribution of the light intensity of illumination emanating from the illumination source 202.

It is recognized herein that the illumination source 202, the multi-axis stage 204, the multi-axis control system 205, the detector 206, the illumination arm 209, the detection arm 211, and the sample stage 212 are similar to the like components of FIG. 2A described previously herein. As such, the description of system 200 should be interpreted to extend to system 300 except where otherwise provided.

In a further aspect, the direct imaging system 301 is communicatively coupled to the computer system 208 of the system 300. In this manner, the direct imaging system 301 may be configured to transmit one or more sets of imagery data to the computer system 208. The sets of imagery data may include imagery data associated with the position of the illumination source 202 or the spatial distribution of the illumination intensity of the light emitted by the illumination source 202. In this manner, the direct imaging system 301 may acquire one or more sets of imagery data of the illumination source 202. Upon acquiring the imagery data of the illumination source 202, the direct imaging system 301 may transmit a signal indicative of the imagery data to the computer system 208.

Upon receiving the imagery data from the direct imaging system 301, the computer system 208 may compare the acquired imagery data of the illumination source 202 to imagery data of the illumination source 202 obtained in a preferred alignment condition. In this sense, the imagery data of the illumination source 202 obtained while the illumination source 202 is in a preferred alignment condition may be referred to as "reference imagery data." For example, the computer system 208 may compare the acquired imagery data of the illumination source 202 to imagery data (i.e., reference imagery data) of the illumination source 202 as it existed in an optimal or near-optimal alignment condition. The comparison data created by comparing the acquired imagery data and the reference imagery data may then be utilized to determine the magnitude and direction of the position drift of the illumination source 202 relative to the various optical element of the optical system 207. In a further aspect, the reference imagery data may be stored in the memory of the computer system 208. In this regard, the acquired imagery data may be compared to the stored reference imagery data in order to measure the amount of position drift and/or the direction of position drift of the illumination source 202. It is recognized herein that the various sets of imagery data described throughout the present disclosure may be stored in the memory of the computer system 208 or a portable memory means (e.g., CD, DVD, flash drive, portable hard drive, communicatively couple server or the like) in any digital image format known in the art.

It is contemplated herein in that the computer system 208 may execute a pre-programmed source position imaging algorithm 305 suitable for comparing the acquired images of the illumination source 202 and the reference images of the illumination source 202. In turn, the source position imaging algorithm 305 may extract magnitude and direction information of the illumination source 202 drift.

Upon determining the magnitude and direction of position drift of the illumination source 202, the computer system 208 may determine a set of position adjustment parameters suitable for use by the multi-axis stage 204 of the multi-axis control system 205. In this sense, the computer system 208 may calculate the adjustment parameters utilizing the determined position drift of the illumination source 202. For example, the computer system 208 may calculate the adjustment parameters required to compensate for the magnitude and direction of the position drift of the illumination source 202. It is recognize herein that the specific form of the adjustment parameters may depend on the specific type of multi-axis actuation stage 204 employed. For instance, in the event an X-Y translational stage is employed, the adjustment parameters may form a set of displacement values in the X- and Y-directions required to compensate for the position drift. In another instance, in a rotational stage setting, the adjustment parameters may, in part, include a rotational component and radial component required to compensate for the position drift of the illumination source 202. It is further contemplated herein that the multi-axis stage 204 may include three-dimensional actuation capabilities. In this setting, the adjustment parameters may include displacement components in three dimensions (e.g., X-direction, Y-direction, and Z-direction).

Upon calculating the set of illumination source position adjustment parameters, the computer system 208 may transmit the set of illumination source 202 position adjustment parameters to the multi-axis actuation control system 205 via the input 203 of the control system 205. In turn, the multi-axis actuation control system 205 system may adjust the position of the multi-axis actuation stage 204 in accordance with the adjustment parameters provided by the computer system 208. In this regard, the adjustment parameters may be used by the control system 205 and the multi-axis stage 204 to compensate for illumination source 202 position drift and/or changes in illumination spatial distribution.

It is further contemplated herein that upon compensating for the illumination source position drift and/or changes in illumination spatial distribution, the system 300 may repeat the source position drift determination sequence described above. In this manner, the computer system 208 may repeat the source position imaging algorithm 305 in an effort to refine the compensation of the illumination source 202 position drift.

In one embodiment, the direct imaging system 301 may include a camera. It is recognized herein that a camera of the direct imaging system 301 may include any camera or camera system known in the art. For example, the camera of the direct imaging system 301 may include a charged coupled device (CCD) base camera.

In another embodiment, the direct imaging system 301 may include a position sensor. It is recognized herein that the position sensor of the direct imaging system 301 may include any position sensor known in the art. For example, the position sensor of the direct imaging system 301 may include a one-dimensional position sensor. By way of another example, the direct imaging system 301 may include a two-dimensional position sensor.

In another embodiment, as depicted in FIG. 3B, the direct imaging system 301 may include two or more cameras or two or more one-dimensional position sensors. For example, a first camera 302a may be arranged perpendicularly with respect to a second camera 302b. By way of a further example, a first positional sensor may be arranged perpendicularly with respect to a second positional. Such an arrangement may allow for the acquisition of both angular and displacement information of the illumination source 202.

It is further recognized herein that the direct imaging system 301 may include one or more optical elements (e.g., focusing lenses 306a and 306b) associated with the optical pathway between the illumination source 202 and each camera 302 of the direct imaging system 301.

In a further embodiment, the direct imagining system 301 may include a camera or position sensor mounted on the optics frame 304 of the system 300 such that camera or position sensor is capable of capturing imagery and/or positional data of the illumination source 202 directly.

In a further embodiment, it is contemplated herein that the direct imaging system 301 may acquire imagery or positional data at a pre-determined time. For example, a user may input a selected data acquisition frequency into the computer 208. At the pre-programmed times, the computer system 208 may then acquire imagery or positional data using the direct imaging system 301. By way of another example, the acquisition time may be determined by the computer system 208 based on an analyzed drift pattern associated with the illumination source 202 and the system 200.

Figure 4A:
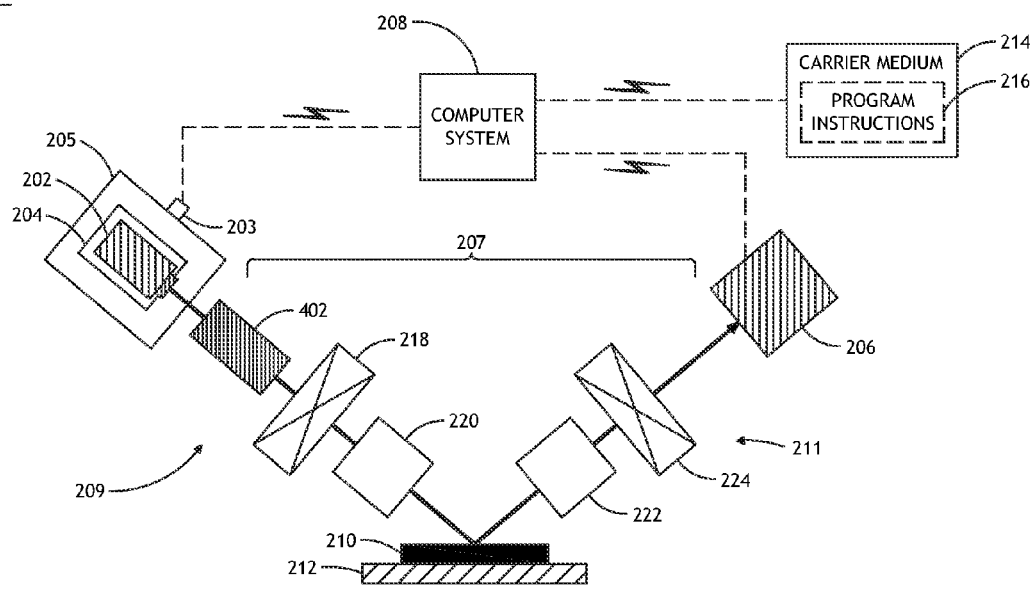
FIG. 4A illustrates a schematic view of a system for tracking and adjusting illumination source position drift in a broadband spectrometer based optical metrology system, in accordance with an alternative embodiment of the present invention.
Figure 4B:
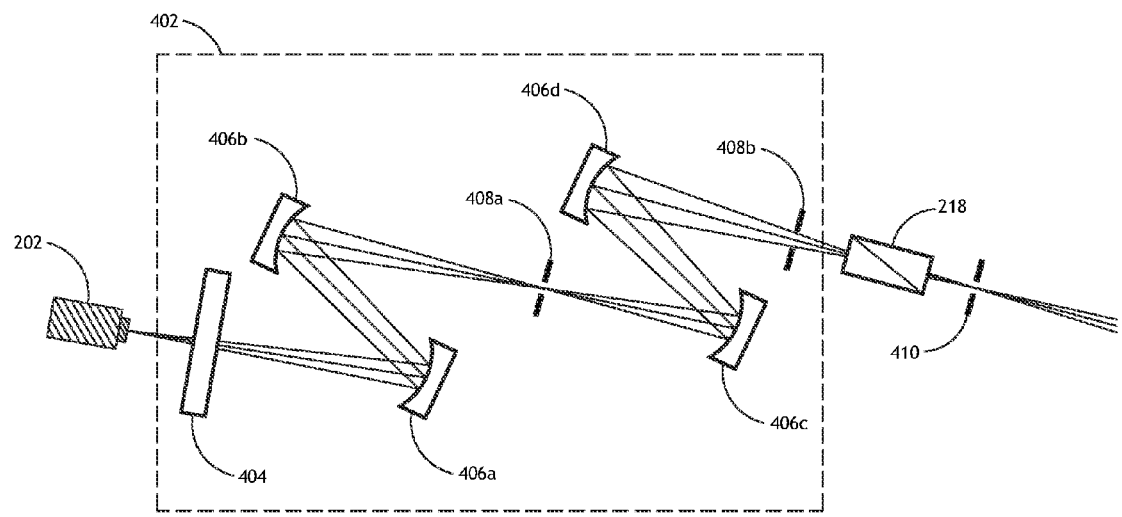
FIG. 4B illustrates a schematic view of a beam condition module suitable for implementation in a system for tracking and adjusting illumination source position drift in a broadband spectrometer based optical metrology system, in accordance with an alternative embodiment of the present invention.

FIGS. 4A and 4B illustrate a schematic view of a system 400 configured to implement beam conditioning module 402, in accordance with an alternative embodiment of the present invention. The term "beam conditioning module" as used throughout the present disclosure may, in the alternative, may be referred to as a "beam conditioner" or an "illuminator."

It is recognized herein that variations in spectral intensity as function of either illumination source position or illumination wavelength may have significant adverse impacts on system performance. This behavior is compounded in settings where intermediate scramblers or homogenizers (e.g., optical fiber-wiggler or optical fiber and the like) are not arranged between the illumination source 202 and an entrance slit of a downstream optical element. Further, it is noted that illumination source 202 non-uniformity as a function of position or wavelength combined with illumination source 202 movement (e.g., drift) relative to the entrance slit of the polarizer 218 may degrade the performance of the system 400. For example, Poynting vector error may be introduced due to a circular trajectory, or "wobbling," of an illumination source 202 relative to a rotating polarizer of the illumination arm 209. This error may lead to illumination beam displacement at the illumination field stop (e.g., see 410 of FIG. 4B). In extreme settings, a plasma-based broadband illumination source exhibiting a large intensity gradient may lead to the introduction of harmonics higher than a theoretical 2ω into the measured signal. It is therefore desirable to introduce a direct-coupled optical system capable of limiting both illumination source 202 position drift, discussed in detail above, and illumination source 202 variation.

It is recognized herein that the illumination source 202, the multi-axis stage 204, the multi-axis control system 205, the detector 206, the illumination arm 209, the detection arm 211, and the sample stage 212 are similar to the like components of FIGS. 2A and 3A described previously herein. As such, the description of system 200 and 300 should be interpreted to extend to system 400 except where otherwise provided. Applicant notes that FIG. 4A illustrates a variation of FIG. 2A of the present disclosure, wherein FIG. 4A incorporates the beam conditional module 402. While not illustrated, it is noted that the system 300 may also be adapted to include a beam conditioning module 402. As such, throughout the present disclosure, it should be noted that the beam conditioning module 402 of the present invention may be implemented in both systems identical to or analogous to systems 200 and/or 300 of the present disclosure.

In one aspect, the beam conditioning module 402 is positioned between the illumination source 202 and the entrance slit of the polarizer 218 (e.g., rotating polarizer) of the illumination arm 209. In a general sense, the beam conditioning module acts to "condition" the light of the illumination path by projecting an image of the illumination source 202 onto a portion of one or more of the optical elements (e.g., slit of polarizing element) such that the projected image has a selected level of uniformity across the projection spot.

In one embodiment, the beam conditioning module 402 of system 400 may be configured to project an image of the illumination source 202 onto an optical element of the illumination arm 209 such that the projected image across a selected area of a given optical element has an intensity level above a selected level. For example, the beam conditioning module 402 may be configured to project an image of the illumination source 202 onto the entrance slit of the polarizer 218 (e.g., rotating polarizer) of the illumination arm 209 such that the intensity of the image is above a sufficient level across the entire area of the entrance slit. In a general sense, it is desirable to maintain the source brightness when forming the illumination source 202 image on the entrance slit of the polarizer 218. As such, the beam conditioning module 402 may be configured to project a source image onto the polarizer 218 slit (or other optical element) such that projected image of the illumination source 202 has an intensity level that is substantially similar to the illumination source 202 intensity level.

In another embodiment, the beam conditioning module 402 of system 400 may be configured to project an image of the illumination source 202 onto an optical element of the illumination arm 209 such that the projected image across a selected area of a given optical element has an intensity gradient level below a selected level. In a general sense, it is desirable to project a uniform illumination source 202 image onto the entrance slit of the polarizer 218 across a broad spectral range. For example, the beam conditioning module 402 may be configured to project an image of the illumination source 202 onto the entrance slit of the polarizer 218 (e.g., rotating polarizer) of the illumination arm 209 such that the intensity gradient of the image is below a selected level across the entire area of the entrance slit across a broad spectral range (e.g., significant portion of spectral range of illumination source 202).

In one embodiment, the beam conditioning module 402 may include one or more mirrors 406a . . . . 406d configured to project an image of the illumination source 202 onto an optical element of the illumination arm 209 such that image has an intensity level above a selected level, while maintaining intensity uniformity (i.e., intensity gradient is below an adequate level). In one aspect, the set of mirrors 406a . . . . 406d of the beam conditioning module 402 may include one or more spherical mirrors. The spherical mirrors of the beam conditioning module 402 may be configured to minimize low spatial frequency scattering. In another aspect, the set of mirrors 406a . . . . 406d of the beam conditioning module 402 may include one or more non-spherical mirrors. It is recognized herein that one or more non-spherical mirrors may be implemented within the beam conditioning module 402 may in order to limit design complexity of the beam condition module 402.

In another embodiment, one or more internal pupil and/or field stops 408a, 408b may be included within in the optical pathway of the beam conditioning module 402 in order to prevent unwanted light from reaching the illumination field stop 410.

The mirrors 406a . . . . 406d of the beam module 402 may be configured to provide magnification greater than unity. In this regard, the mirrors 406a . . . . 406d may be utilized to magnify the image of the illumination source 202 such that only the "sweet spot" (i.e., portion of illumination distribution having highest intensity level) passes through the illumination field stop 410.

It is recognized herein that several factors may be considered when determining the degree of magnification of the beam condition module 402. For example, the chosen degree of magnification may depend on the size of the illumination beam sought to be implemented, the illumination uniformity required for the given application (i.e., metrology system specifications), and the polarizer 218 slit size, among other factors.

Further, as shown in FIG. 4B, the projection of the sweet spot onto the polarizer slit may be accomplished with manageable spectral angular distribution by projecting the illumination source 202 image at near normal incidence (e.g., via mirrors 406a . . . . 406d) to downstream optical elements (e.g., polarizer 218) in a given oblique incidence metrology tool.

In another aspect, the angle of incident of illumination and the relative orientation of the various optical components (e.g., mirrors 406a . . . . 406d) may be selected and configured to provide an illumination beam with residual polarization below a selected level. In this regard, the beam conditioning module 402 may be configured to minimize residual polarization via implementation of a low angle of incidence optical design and selected relative orientations of the various optical components such that birefringence induced by the optical coatings of the various optical components of the beam conditioning module 402 is below a selected level (e.g., birefringence is minimized). Those skilled in the art will recognize that coating induced birefringence is dependent upon both the angle of incidence of illumination relative to a coating surface and the thickness of the coating thickness.

Figure 5:
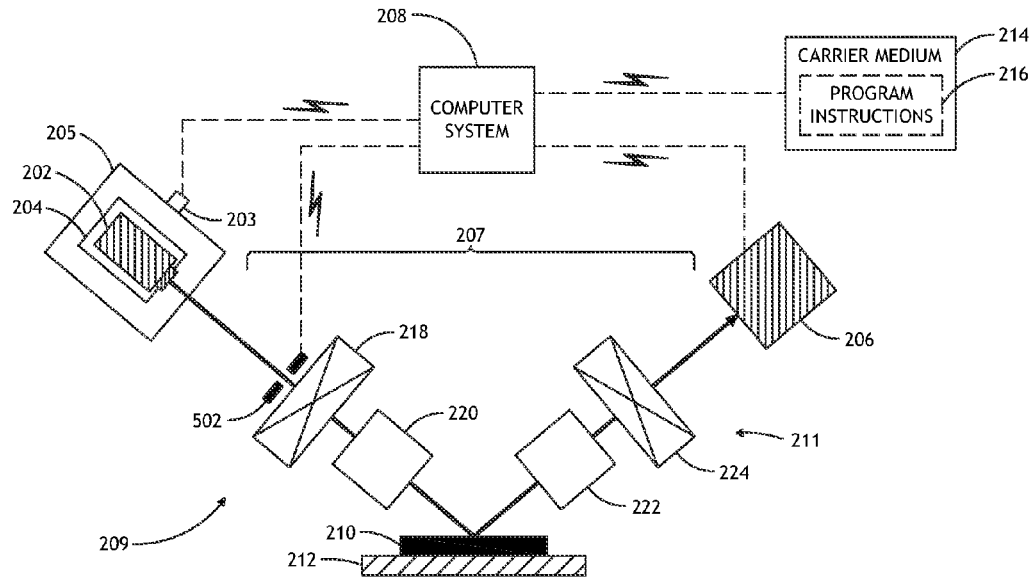
FIG. 5 illustrates a schematic view of a system for tracking and adjusting illumination source position drift in a broadband spectrometer based optical metrology system, in accordance with an alternative embodiment of the present invention.

FIG. 5 illustrates a schematic view of a system 500 configured to implement an adjustable polarization slit 502, in accordance with an alternative embodiment of the present invention. In one aspect, the adjustable polarization slit 502 is positioned along the illumination arm 209 of the optical system 207 between the illumination source 202 and the polarizer 218. The adjustable polarization slit 502 may be utilized by the system 500 in order to adjust the size of the polarization slit 502 to a size providing adequate illumination beam uniformity. In this sense, the adjustable polarization slit 502 may be utilized to isolate the sweet spot of the illumination beam from the less intense and less uniform portions of the illumination beam. It is recognized herein that the amount of adjustment required may depend on several factors, such as, but not limited to, required illumination beam brightness and required intensity uniformity of the system 500.

The adjustable polarization slit 502 may include any adjustable polarization slit 502 known in the art. For example, the adjustable polarization slit 502 may include an adjustable polarization slit capable of adjustment in one dimension. For instance, the adjustable polarization slit 502 may include an adjustable polarization slit capable of adjusting the slit height or the slit width. By way of another example, the adjustable polarization slit 502 may include an adjustable polarization slit capable of adjustment in two dimensions. For instance, the adjustable polarization slit 502 may include an adjustable polarization slit capable of adjusting the slit height and the slit width. It is contemplated herein that a four knife edge based adjustable slit I suitable for adjusting the slit size in two dimensions.

In one embodiment, the adjustable polarization slit 502 may include an adjustable polarization slit 502 driven by one or motorized micrometers. It is recognized herein that any motorized micrometer known in the art is suitable for implementation in the present invention. In another embodiment, the adjustable polarization slit 502 may include an adjustable polarization slit 502 driven by one or more piezoelectric actuators. It is recognized herein that any piezoelectric actuator known in the art is suitable for implementation in the present invention.

In one aspect, the adjustable polarization slit 502 may be communicatively coupled to the computer system 208. In this sense, the adjustable polarization slit 502 may be configured to receive instruction signals from the computer system 208. In one embodiment, the computer system 208 may transmit instructions to the adjustable polarization slit 502 based on results from a source position diagnostic algorithm 217, as discussed in greater detail above. In this manner, the source position diagnostic algorithm 217 may be configured to incorporate the ability to adjust the polarization slit height or width when determining the position adjustment parameters for the multi-axis stage 204. In this sense, the computer system 208 may supply adjustment parameters to either the multi-axis stage 204 or the adjustable polarization slit 502 or both based on the source position diagnostic algorithm 217 executed by the computer system 208.

In another embodiment, the computer system 208 may transmit instructions to the adjustable polarization slit 502 based on results from a source position imaging algorithm 305, as discussed in greater detail above. In this manner, the source position imaging algorithm 305 may be configured to incorporate the ability to adjust the polarization slit height or width when determining the position adjustment parameters for the multi-axis stage 204. In this sense, the computer system 208 may supply adjustment parameters to either the multi-axis stage 204 or the adjustable polarization slit 502 or both based on the source position imaging algorithm 305 executed by the computer system 208.

In another embodiment, the computer system 208 may transmit instruction to the adjustable polarization slit 502 based on user input. In this manner, a user may enter instructions into the computer system 208 via one or more user interfaces (not shown). Then, the computer system 208 may transmit corresponding instruction signals to the adjustable polarization slit 502. In a further embodiment, user input may be combined with the results of the source position diagnostic algorithm 217 or the source position imaging algorithm 305 by the computer system 208 in order to achieve improved illumination characteristics of the system 500.

It is further contemplated herein that the adjustable polarization slit 502 may be implemented in conjunction with the beam condition module 402, providing for even greater control of illumination source brightness and intensity uniformity. In this sense, although not shown, the beam conditioning module 402 may be positioned between the illumination source 202 and the entrance of the adjustable polarization slit 502.

Figure 6:
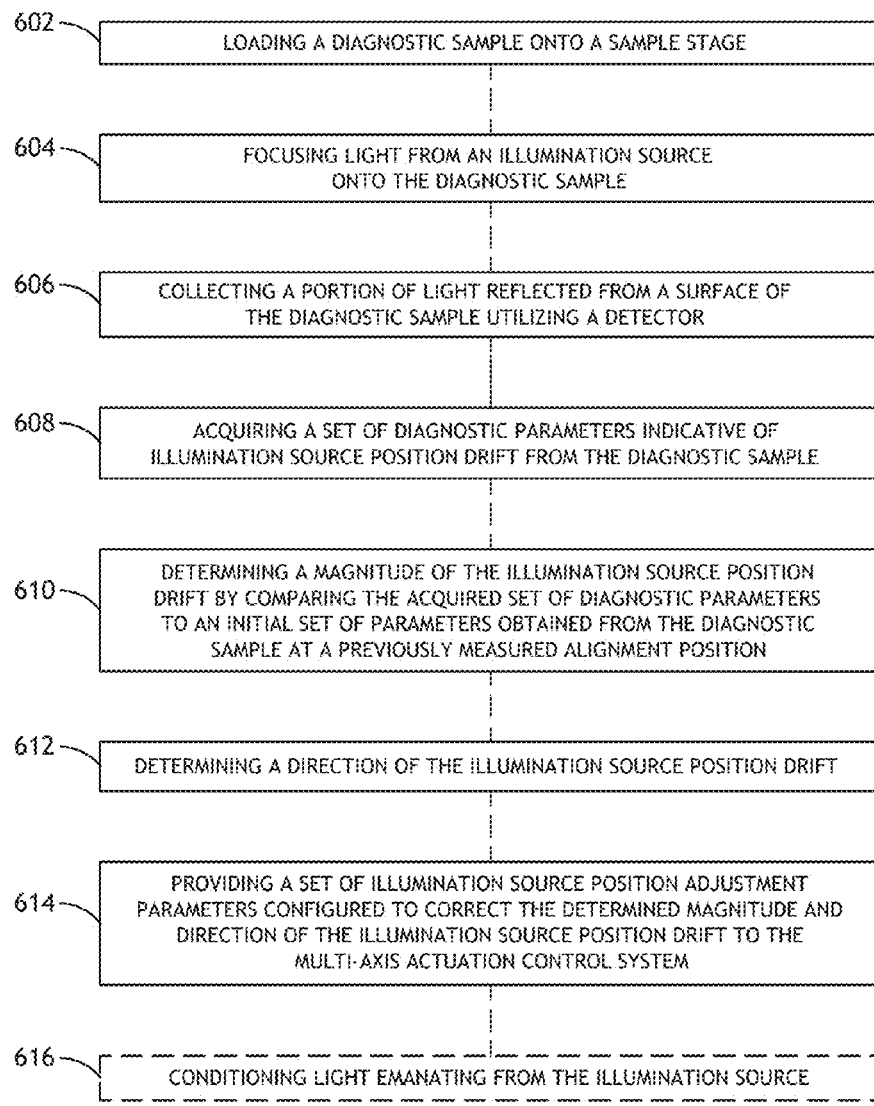
FIG. 6 is a flow diagram illustrating a method for tracking and adjusting illumination source position drift in a broadband spectrometer based optical metrology system, in accordance with one embodiment of the present invention.

FIG. 6 illustrates a process flow 600 suitable for implementation by the system 200 of the present invention. In step 602, a diagnostic sample is loaded onto a sample stage. In step 604, light from an illumination source disposed on a multi-axis stage is focused onto the diagnostic sample. In step 606, a portion of light reflected from a surface of the diagnostic sample is collected utilizing a detector, wherein the illumination source and the detector are optically direct-coupled via an optical system. In step 608, a set of diagnostic parameters indicative of illumination source position drift are acquired from the diagnostic sample. In step 610, a magnitude of the illumination source position drift is determined by comparing the acquired set of diagnostic parameters to an initial set of parameters obtained from the diagnostic sample at a previously measured alignment condition. In step 612, a direction of the illumination source position drift is determined. In step 614, a set of illumination source position adjustment parameters configured to correct the determined magnitude and direction of the illumination source position drift is provided to the multi-axis actuation control system of the multi-axis stage. In a further step 616, light emanating from the illumination source is conditioned (e.g., conditioned via beam conditioning module or conditioned via adjustable polarizer slit).

Figure 7:
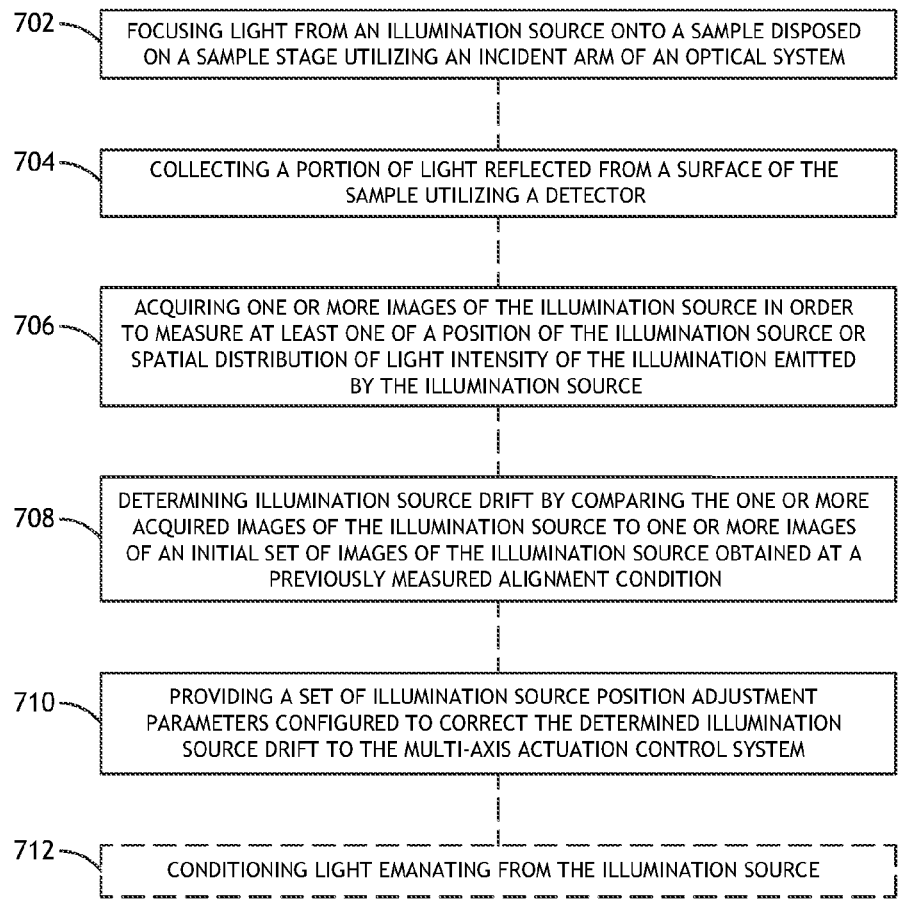
FIG. 7 is a flow diagram illustrating a method for tracking and adjusting illumination source position drift in a broadband spectrometer based optical metrology system, in accordance with an alternative embodiment of the present invention.

FIG. 7 illustrates an alternative process flow 700 suitable for implementation by the system 300 of the present invention. In step 702, light from an illumination source is focused onto a sample disposed on a sample stage. In step 704, a portion of light reflected from a surface of the sample is collected utilizing a detector, the illumination source and the detector being optically direct-coupled via an optical system. In step 706, one or more images of the illumination source are acquired in order to measure at least one of a position of the illumination source or a spatial distribution of light intensity of the illumination emitted by the illumination source. In step 708, illumination source drift is determined by comparing the one or more acquired images of the illumination source to an initial set of images of the illumination source obtained at a previously measured alignment condition. In step 710, a set of illumination source position adjustment parameters configured to correct the determined illumination source drift is provided to the multi-axis actuation control system. In step 712, light emanating from the illumination source is conditioned (e.g., conditioned via beam conditioning module or conditioned via adjustable polarizer slit)

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. An apparatus for tracking and adjusting illumination source position drift in a broadband spectrometer based optical metrology system, comprising:
   a broadband spectrometer including:
      a multi-axis actuation control system;
      an illumination source disposed on a multi-axis actuation stage of the multi-axis actuation control system;
      a detector, wherein the detector is configured to collect at least a portion of light reflected from a surface of a sample disposed on a sample stage, the sample stage configured to receive at least a diagnostic sample, the diagnostic sample having a set of properties configured to produce a known optical response within the broadband spectrometer as a function of illumination source position drift;
      an optical system including an illumination arm and a detection arm, the illumination source and the detector being optically direct-coupled by the optical system, wherein the illumination arm is configured to focus light emanating from the illumination source onto the surface of the diagnostic sample, wherein the detection arm is configured to transmit a portion of light reflected from the surface of the removable diagnostic sample to the detector, the illumination arm including a polarizing element and one or more optical focusing elements, the detection arm including an analyzing element and one or more optical collection elements; and
   a computer system communicatively coupled to the multi-axis actuation control system and the detector, wherein the computer system is configured to:
      acquire a set of broadband spectroscopic diagnostic parameters including at least one of one or more thin film parameters or one or more grating parameters from the diagnostic sample disposed on the sample stage, wherein the set of broadband spectroscopic diagnostic parameters are indicative of position drift of the illumination source as measured relative to one or more components of the optical system;
      determine a magnitude of illumination source position drift by comparing the acquired set of broadband spectroscopic diagnostic parameters to an initial set of broadband spectroscopic parameters obtained from the diagnostic sample at a previously measured alignment condition;
      determine a direction of illumination source position drift; and
      provide a set of illumination source position adjustment parameters configured to correct the determined magnitude and direction of the illumination source position drift to the multi-axis actuation control system.

2. The apparatus of claim 1, wherein the multi-axis actuation stage comprises at least one of a multi-axis translational stage or a multi-axis rotational stage.

3. The apparatus of claim 1, wherein the computer system is configured to determine a direction of illumination source position drift by transmitting a set of command signals to the multi-axis actuation control system in order to translate the illumination source by the determined magnitude along a first direction and a second direction orthogonal to the first direction.

4. The apparatus of claim 1, further comprising:
   a conditioning module positioned between the illumination source and the polarizing element of the illumination arm, wherein the conditioning module is configured to project an image of the illumination source having a selected level of uniformity onto a portion of one or more optical elements of the illumination arm.

5. The apparatus of claim 4, wherein the conditioning module is configured to project an image of the illumination source having an intensity gradient below a selected level onto a portion of one or more optical elements of the illumination arm.

6. The apparatus of claim 4, wherein the conditioning module is configured to project an image of the illumination source having an intensity level above a selected intensity level across a selected wavelength range onto a portion of one or more optical elements of the illumination arm.

7. The apparatus of claim 4, wherein the condition module comprises:
   a conditioning module configured to project an image of the illumination source onto a slit of the polarizing element of the illumination arm.

8. The apparatus of claim 1, further comprising:
   an adjustable optical slit positioned between the illumination source and the polarizing element of the illumination arm, the adjustable optical slit being communicatively coupled to the computer system, wherein the adjustable slit is configured to adjust in response to instructions received from the computer system.

9. The apparatus of claim 1, wherein the illumination source comprises:
   at least one broadband illumination source.

10. The apparatus of claim 1, wherein the polarizing element of the illumination arm of the optical system comprises:
    a rotating polarizer.

11. The apparatus of claim 1, wherein the set of broadband spectroscopic diagnostic parameters are acquired by the computer system via a diagnostic sequence, wherein the diagnostic sequence is configured to decouple illumination source intensity decay and one or more changes to a sample property from the illumination source position drift.

12. The apparatus of claim 1, wherein the initial set of parameters are acquired by the computer system utilizing imagery data of the diagnostic sample collected at a selected alignment condition.

13. A method for tracking and adjusting illumination source position drift in a broadband spectrometer based optical metrology system, comprising:
   loading a diagnostic sample onto a sample stage of a broadband spectrometer, the diagnostic sample having a set of properties configured to produce a known optical response within the broadband spectrometer as a function of illumination source position drift;
   focusing light from an illumination source disposed on a multi-axis stage onto the diagnostic sample;
   collecting a portion of light reflected from a surface of the diagnostic sample utilizing a detector, wherein the illumination source and the detector are optically direct-coupled via an optical system;

acquiring a set of broadband spectroscopic diagnostic parameters indicative of illumination source position drift from the diagnostic sample, wherein the set of broadband spectroscopic diagnostic parameters include at least one of one or more thin film parameters or one or more grating parameters;

determining a magnitude of the illumination source position drift by comparing the acquired set of broadband spectroscopic diagnostic parameters to an initial set of parameters obtained from the diagnostic sample at a previously measured alignment condition;

determining a direction of the illumination source position drift; and providing a set of illumination source position adjustment parameters configured to correct the determined magnitude and direction of the illumination source position drift to the multi-axis actuation control system of the multi-axis stage.

14. The method of claim 13, further comprising:
adjusting a position of the illumination source utilizing the provided set of illumination source position adjustment parameters utilizing the multi-axis stage of the multi-axis control system.

15. The method of claim 13, further comprising:
adjusting a position of the illumination source utilizing the provided set of illumination source position adjustment parameters utilizing the multi-axis stage of the multi-axis control system;

upon adjustment of the position of the illumination source, acquiring a second set of diagnostic parameters indicative of illumination source position drift from the diagnostic sample;

determining a magnitude of an uncompensated illumination source position drift by comparing the acquired second set of diagnostic parameters to an initial set of parameters obtained from the diagnostic sample at a previously measured alignment condition;

determining a direction of the uncompensated illumination source position drift; and providing a second set of illumination source position adjustment parameters configured to correct the determined magnitude and direction of the uncompensated illumination source position drift to the multi-axis actuation control system of the multi-axis stage.

16. The method of claim 13, further comprising:
conditioning light emanating from the illumination source.

17. The apparatus of claim 1, wherein the broadband spectrometer comprises:
at least one of a broadband spectral ellipsometer, a broadband spectral scatterometer, a polarized spectral reflectometer or an unpolarized spectral reflectometer.

18. The apparatus of claim 1, wherein the diagnostic sample comprises:
at least one of a diagnostic thin film sample or a diagnostic patterned grating sample.

19. The method of claim 13, wherein the broadband spectrometer comprises:
at least one of a broadband spectral ellipsometer, a broadband spectral scatterometer, a polarized spectral reflectometer or an unpolarized spectral reflectometer.

20. The method of claim 13, wherein the diagnostic sample comprises:
at least one of a diagnostic thin film sample or a diagnostic patterned grating sample.

21. An apparatus for tracking and adjusting illumination source position drift in a broadband spectrometer based optical metrology system, comprising:

a broadband spectrometer including a multi-axis actuation control system and a detector, wherein the broadband spectrometer is configured to focus light from an illumination source onto a surface of a diagnostic sample, wherein the broadband spectrometer is further configured to transmit a portion of light reflected from the surface of the diagnostic sample to the detector; and a computer system communicatively coupled to the multi-axis actuation control system and the detector, wherein the computer system is configured to:

acquire a set of broadband spectroscopic diagnostic parameters including at least one of one or more thin film parameters or one or more grating parameters from the diagnostic sample, wherein the set of broadband spectroscopic diagnostic parameters are indicative of position drift of the illumination source;

determine a magnitude of illumination source position drift by comparing the acquired set of broadband spectroscopic diagnostic parameters to an initial set of broadband spectroscopic parameters obtained from the diagnostic sample at a previously measured alignment condition;

determine a direction of illumination source position drift; and provide a set of illumination source position adjustment parameters configured to correct the determined magnitude and direction of the illumination source position drift to the multi-axis actuation control system.

* * * * *